United States Patent [19]
Dawson

[11] Patent Number: 5,914,119
[45] Date of Patent: Jun. 22, 1999

[54] PROCESS AND PRODUCT FOR ATTRACTING ANIMALS AND COVERING HUMAN SCENT

[76] Inventor: Richard A. Dawson, 472 Nine Mile Rd., NE., Comstock Park, Mich. 49321

[21] Appl. No.: 08/766,973
[22] Filed: Dec. 16, 1996

Related U.S. Application Data

[63] Continuation of application No. 08/259,540, Jun. 14, 1994, Pat. No. 5,618,548.
[51] Int. Cl.$^6$ .................................................. A01N 25/00
[52] U.S. Cl. ........................................... 424/405; 424/40
[58] Field of Search ....................... 424/405, 40; 119/171

[56] References Cited

U.S. PATENT DOCUMENTS 3,795,999  3/1974  Tabita ........................................ 424/40
5,415,131  5/1995  Dodman ................................... 119/171

Primary Examiner—Neil S. Levy
Assistant Examiner—William E. Benston, Jr.
Attorney, Agent, or Firm—Waters & Morse, PC; John A. Waters

[57] ABSTRACT

An improved animal lure and cover scent process and product employs a combustible absorbent material impregnated with an aromatic substance having fragrance attractive to an animal, with the absorbent material being of restricted combustibility such that the absorbent material tends to smoke without producing a flame as it burns, the smoke entraining the fragrance with it as it travels through the air. The combustible absorbent material of the present invention is in the form of an incense stick wherein a cellulosic material formed from sawdust is coated on one end of a combustible bamboo stick. A weather shield protects the incense stick from wind and rain.

22 Claims, 2 Drawing Sheets

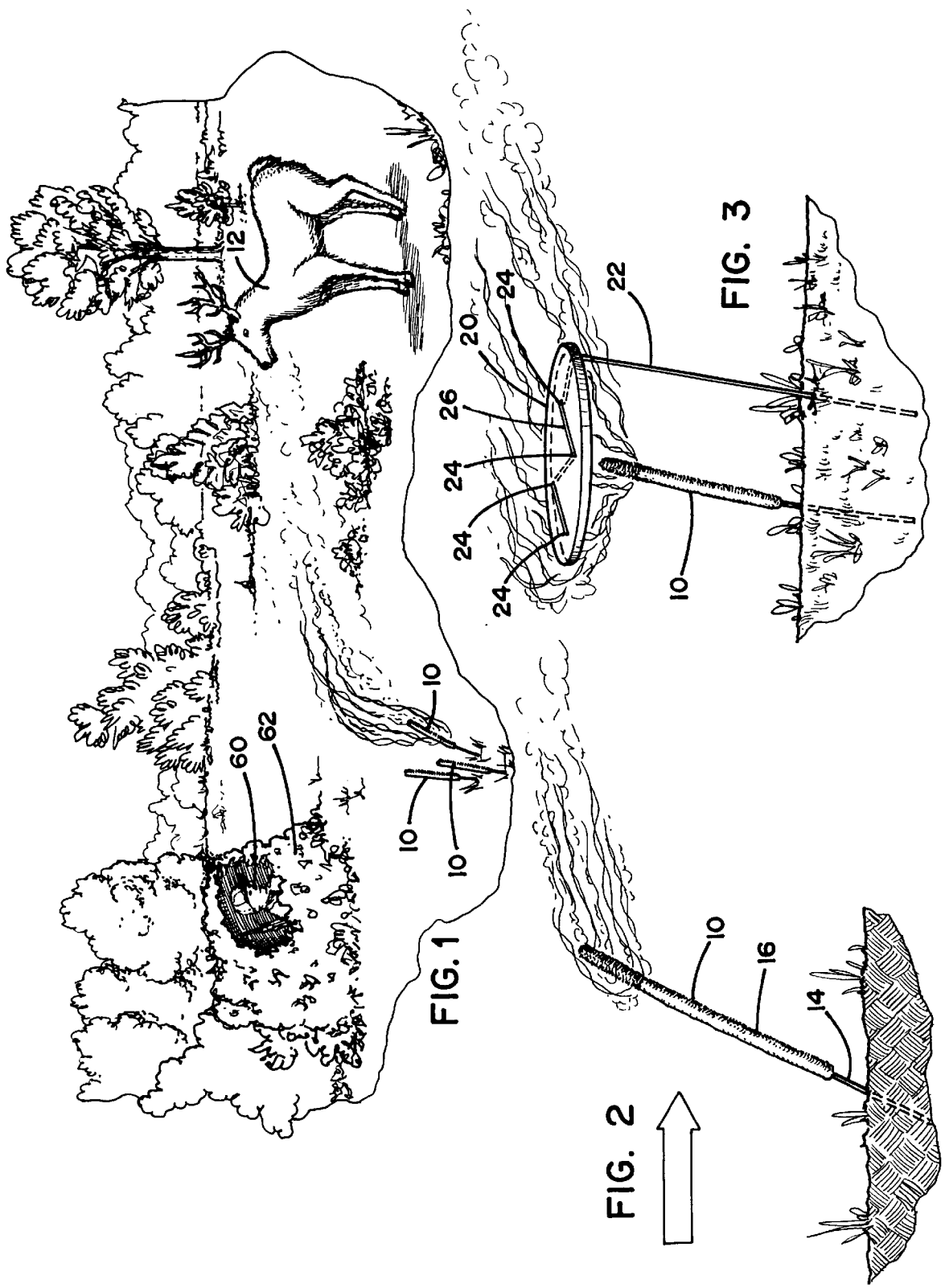

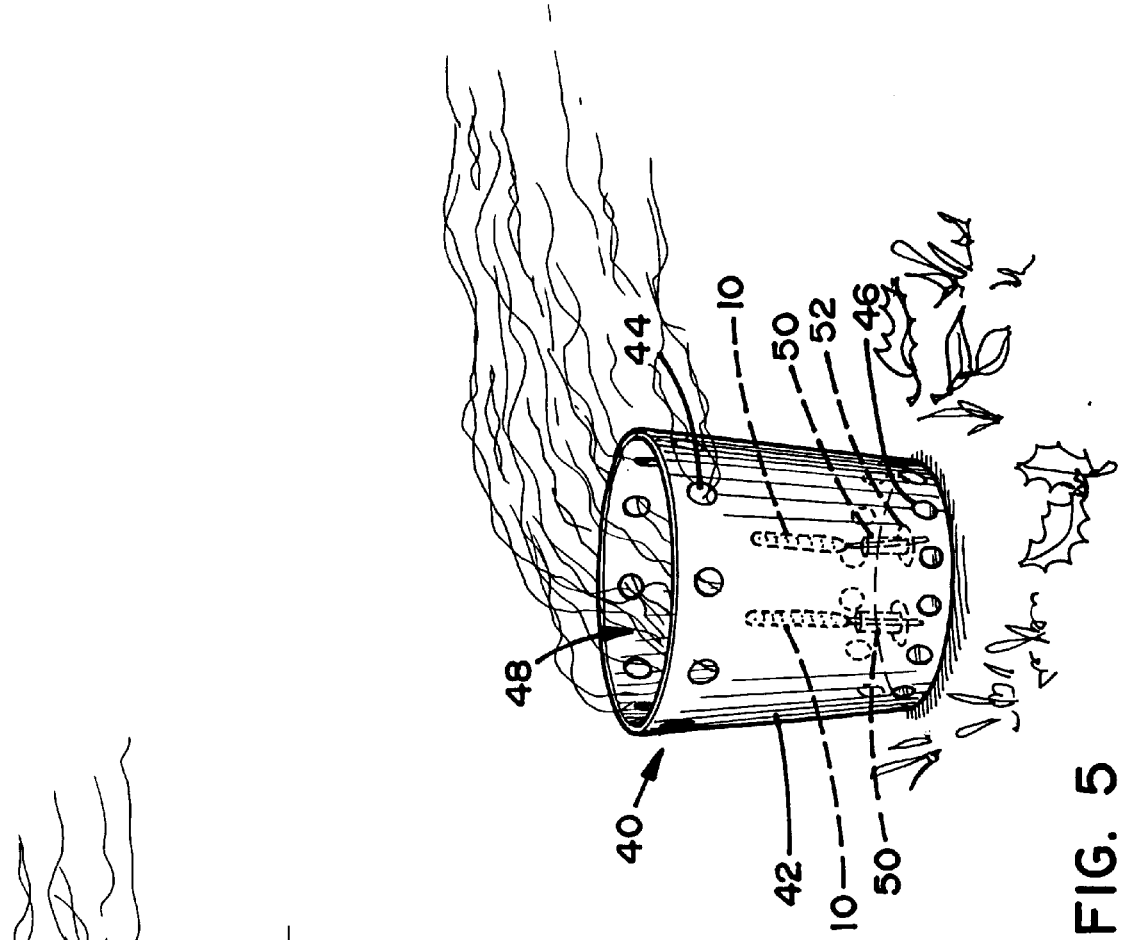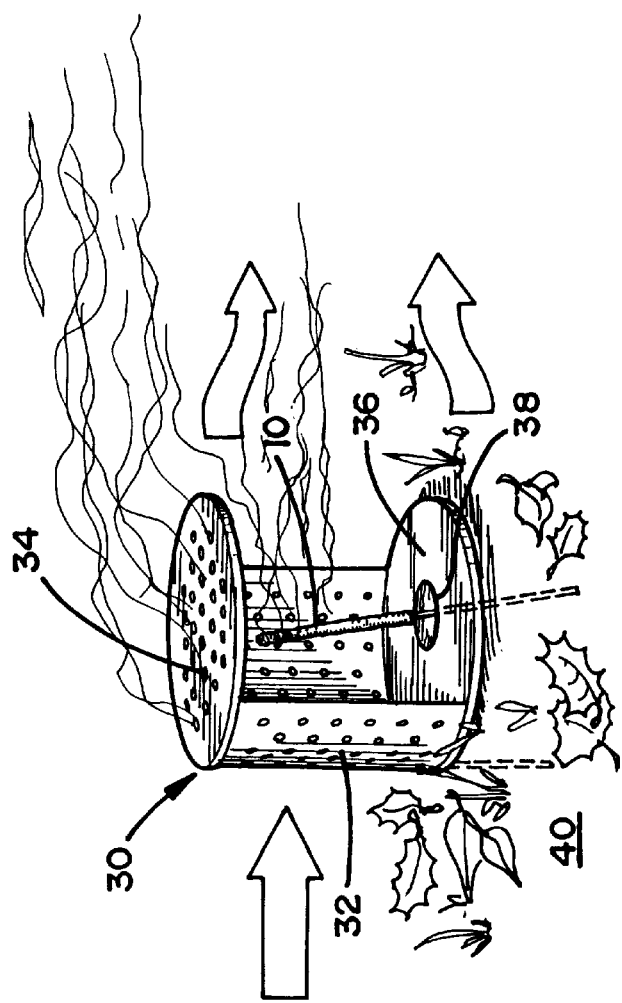
FIG. 4
FIG. 5

PROCESS AND PRODUCT FOR ATTRACTING ANIMALS AND COVERING HUMAN SCENT

This is a continuation of application Ser. No. 08/259,540, entitled PROCESS AND PRODUCT FOR ATTRACTING ANIMALS AND COVERING HUMAN SCENT and filed on Jun. 14, 1994, now U.S. Pat. No. 5,618,548.

BACKGROUND OF THE INVENTION

Wild game hunting is a popular sport, and hunters have devised numerous products and methods in order to improve the hunter's odds against the animal. While the hunter has superior fire power, animals possess a number of natural defenses that help to even the odds. One of these is a highly refined sense of smell that makes it possible for many animals to detect the presence of a human being at great distances, at least in a downwind direction. To overcome this disadvantage, a number of products have been developed that are designed to either cover the scent of a human being or to actually provide an attractive smell to an animal, such as a deer. These substances may include one or a combination of natural and/or synthetic animal urine or natural or synthetic aromatic substances that simulate fruits or vegetables or other things to which a deer or other animals may be attracted. Some of these products work, at least to some extent, but they generally have limited effectiveness.

One of the problems with existing products on the market is that the smell does not carry well enough or far enough or last long enough to provide maximum beneficial effect. One way of dispersing the aromatic substance is to dissolve it in a highly volatile liquid such as alcohol and then permit the alcohol to evaporate. The rate of evaporation can be increased by heating the liquid. Evaporation, however, is dependent on temperature, with evaporation occurring much more slowly at cold temperatures. Rainy weather also impairs evaporation. Wind, another factor, can also vary the rate of evaporation. Under most circumstances, evaporation occurs too slowly for maximum beneficial effect.

Conventional wisdom is that deer and other animals react highly negatively to the scent of a human being and any other scent indicative of the presence of a human being. Smoke is usually associated with the presence of human beings, and conventional wisdom has it that the scent of smoke in the air will serve as an indication to a game animal that a human being is present and will cause the animal to stay away. Thus, while prior liquid scents have been heated, they have not been dispersed by burning the carrier.

The object of the present invention is to provide an improved animal lure and cover scent that disperses broadly and widely in any temperature condition and provides a fragrance or scent that masks the scent of a human being and serves to attract animals to the location of the deer lure.

SUMMARY OF THE INVENTION

In accordance with the present invention, an improved animal lure and cover scent comprises a combustible absorbent material impregnated with a fragrance that is attractive to an animal and covers the scent of human beings, with the absorbent material being of restricted combustibility such that the absorbent material can be induced to smolder and produce smoke without producing a continuous flame as it burns, the smoke entraining the fragrance with it as it travels through the air.

The combustible absorbent material of the present invention desirably is an incense stick wherein a cellulosic combustible bamboo stick. The cellulose material is porous and is combined with one or a combination of natural material formed from sawdust is coated on one end of a and/or synthetic aromatic substances having a smell that is attractive to a deer or other animal. A particularly desirable fragrance is the fragrance of urine. Another highly desirable fragrance is the fragrance of apples. Other fragrances that are found to be attractive to animals are fragrances that simulate sweet corn, field corn, soy beans, red oak acorns, white oak acorns, peanut butter, anise, pumpkin, over-ripe apples, molasses, carrots, and dead fish.

The incense sticks are formed in a conventional manner but are larger than the stick typically used for incense in the United States so that they will burn for up to two hours. The fragrance oils incorporated into the incense sticks preferably are dispersed in a liquid agent having low volatility so that the fragrance is not given off readily at ambient temperatures but is gradually released under the heated conditions of the burning incense stick.

Another aspect of the present invention is a shield for protecting the burning incense stick from rain or wind. One shield has a perforated arcuate wall that is positioned upwind of the incense stick and has a cover that extends over the incense stick. The downwind side of the shield is open. The shield desirably can be formed from a coffee can or the like. Another shield employs only the cover and not the wind baffle. A third shield comprises a perforated bucket that provides wind protection from all directions.

These and other objects, advantages, and features of the invention are disclosed in more detail in connection with a description of the preferred embodiments of the present invention set forth below.

DESCRIPTION OF THE DRAWINGS

FIG. 1 is a pictorial view showing the use of the present invention in attracting a deer.

FIG. 2 is a side elevational view of the deer lure of the present invention.

FIG. 3 is a perspective view showing the use of a weather shield protective device with the present invention.

FIG. 4 is a perspective view showing the use of a second type of weather shield protective device with the present invention.

FIG. 5 is a perspective view showing the use of another type of weather shield protective device with the present invention.

DESCRIPTION OF THE PREFERRED EMBODIMENTS

Referring now to the drawings, an animal lure 10 (which is also a human cover scent) constructed in accordance with the present invention is shown in use in FIG. 1 and is shown in more detail in FIG. 2. The animal lure is useful for attracting animals such as whitetail deer 12 and a variety of other animals, including moose, elk, mule deer, European deer, fallow, sika and other deer species, mountain goats, mountain sheep, turkey and bear. For convenience, the invention will be described as it is used in connection with attracting deer. Substantially the same method is used for attracting other animals as well.

Deer lure 10 desirably is in the form of an incense stick formed of a wood (preferably bamboo) shaft 14 covered at an outer end with an absorbent combustible material 16, preferably a form of sawdust. The sawdust material is reduced to a spongy cellulose form when it is formed on the outer end of the bamboo stick. The incense stick is produced in a conventional manner, and these are available commercially. In the present invention, the sawdust material 16 is about a ¼ to 5⁄16 inches in diameter and extends for about 7½–8 inches along a stick that is 10–11 inches long. With this amount of material, the stick can burn for up to about two hours, depending on wind and other conditions. Larger sticks can be employed.

The sawdust material is porous and serves as means for retaining aromatic oils in the incense stick.

The porous combustible sawdust material on the incense stick is impregnated with aromatic oils of a fragrance that are designed to cover the scent of human beings and/or attract deer or the appropriate animals when released by the heat produced by the burning of the stick. The aromatic oils are formed of natural or synthetic substances or a combination of both. Fragrance companies have had substantial luck in identifying the active ingredients in natural substances and have been able to duplicate natural materials with synthetic materials with some success in recent times. The aromatic substances used to impregnate the incense stick of the present invention are produced by dispersing aromatic oils in a liquid diluent and thereafter applying the liquid material to the incense sticks so that the liquid is absorbed into the porous structure of the incense stick.

The fragrances of the present invention are formulated with diluents that reduce the concentration of the aromatic substance. Known diluents may be used. These include alcohol or a glycol, such as dipropylene glycol (DPG) or diethylene glycol or other known substances. The glycols are preferred over alcohol because they are less volatile. A less volatile diluent is preferred because it increases the shelf life of the product and limits the release of fragrances under ambient temperatures, while at the same time providing a gradual but substantial release of fragrances under the heated conditions present when the incense stick is burned. Because of this, higher molecular weight DPG is preferred. A more volatile carrier liquid such as alcohol may be used in connection with the glycol for purposes of applying the fragrance to the stick and permitting the fragrance to penetrate the porous material on the stick. The alcohol carrier material evaporates quickly, leaving the aromatic oils and any less volatile diluent in the stick in a more concentrated form.

The concentration of the aromatic oils is an important feature of the present invention and distinguishes other deer lure and incense products. In typical deer lure products relying on evaporation, the aromatic substances are diluted by alcohol to a level of about 20% or less. The aromatic substances constitute 30 to 60% of the incense of the present invention and sometimes even a higher percentage. This higher concentration makes the product much more effective.

The fragrance material of the present invention can have a flash point of about 90–250° F. and more typically about 140–200° F. There is some natural evaporation of the material at ambient temperatures, but the product has a long shelf life and provides a gradual release of the aroma at the increased temperatures present when the stick is ignited.

The use of conventional incense sticks is desirable in the present invention, because bamboo smoke is believed to have little natural odor when it burns or at least is easily covered by the fragrance of the aromatic oils in the incense stick.

In use, a deer lure incense stick is first ignited with a match or the like. This produces a flame. The flame is blown out, and the stick thereafter continues to smolder and smoke until it burns completely, with the flame not returning. Thus, there is a gradual heat that accelerates release of the aroma, and there are smoke molecules for the aroma to cling to for dispension of the aroma. There is no continuous flame, however, which would tend to burn the aromatic oils.

When aromatic oils are dispersed in smoke in a burning incense stick, surprising results are achieved. The aroma seems to cling to the smoke particles and attaches to anything it comes in contact with, including leaves, trees, and the hunters clothing. The smoke and aroma travels great distances. The aroma has been detected by human senses at a distance of at least 600 yards away. Prior art liquids are undetectable at much more than 30 yards away from the source. Moreover, the smell of the present invention lasts for a long time. An area in which an incense stick has been burned retains the smell even after the incense stick is burned.

In tests with animals, it has been found that animals are not repelled by the smoke but are instead attracted by the aromatic smoke produced by the present invention. The fact that the aromatic oils are dispersed with smoke does not appear to be a negative factor at all, but instead appears to be a positive factor. The smoke not only attracts deer, but it also camouflages and makes undetectable the normal scent of human beings. Thus, animals are attracted from a downwind condition (where they would normally detect the human odor) as well as an upwind condition, wherein some of the odor from smoke usually travels. Typical conditions involve changes in wind conditions and swirling winds to some extent. This causes the odor of smoke to be detectable in all directions from a source of smoke.

A number of fragrances have been found to work successfully in attracting different types of animals. These fragrances include urine, apples, sweet corn, field corn, red oak acorns, white oak acorns, soy beans, peanut butter, anise, pumpkin, over-ripe apples, molasses, carrots, and dead fish. The urine fragrance is quite strong and can be desirably softened by burning two incense sticks at once, a urine stick and an apple stick. This seems to have a desirable effect. Fragrances are available commercially.

As stated above, a wide variety of animals have been found to be attracted by the incense sticks of the present invention.

The use of smoke sticks or incense sticks has been found to be a desirable and convenient way to disperse the aromatic fragrances of the present invention. However, it is contemplated that other forms of porous, combustible materials that produce smoke without a continuous flame would be a successful vehicle for dispensing animal attracting fragrances, the important factor being that the fragrances are dispersed from a smoldering combustible material along with the smoke.

The incense sticks of the present invention are used by placing the stem of the incense stick in the ground and igniting the stick. The smoke then wafts into the air and travels great distances, attracting animals. Desirably, a number of sticks are placed in the ground at the same time, with only one or two sticks being ignited at once. A combination of one urine stick and one apple stick has been found to be particularly effective with deer.

Safe utilization of the present invention dictates that an area be cleared around the incense stick of about three feet in diameter down to bare earth. The ground conditions can be made to look like a deer "scrape", which is an area of about three feet in diameter that a buck clears with his hooves and urinates on in order to stake out his territory.

Because the incense sticks of the present invention are designed to smolder and smoke and not burn with an open flame (once the initial flame is blown out), the sticks can be somewhat sensitive to wind and rain. Therefore, weather shields have been developed in accordance with the present invention. As shown in FIG. 3, a rain shield 20 (which can be the metal lid of a coffee can) is positioned above a burning incense stick by means of a metal rod 22. The metal rod has a lower end that protrudes into the ground and an upper end that is bent in a zigzag fashion and threaded through openings 24 in the lid. The rod can be a coat hanger.

Another type of weather shield 30 is shown in FIG. 4. This device can be formed out of a can, such as a coffee can or the like, with the axis of the can being perpendicular to the ground. Weather shield 30 comprises a perforated arcuate section 32 (a wall of the can) that is positioned to face the wind, with a perforated cover being attached to the top of the arcuate section and a bottom being positioned on the bottom of the arcuate section. The incense stick 10 extends through an opening 38 in bottom 36 into the ground 40. Wind traveling in the direction of the arrows hits arcuate section 32, which serves as a baffle, and is diverted away from the incense stick. Top 34 serves as a rain protector for the incense stick.

In FIG. 5, weather shield 40 is in the form of a bucket 42, which can be a conventional two and one-half to five gallon plastic bucket. Upper openings 44 and lower openings 46 are formed around the upper and lower peripheries of cylindrical side walls of the bucket. Combustion ventilation enters the bucket through openings 46 at the bottom of the bucket, and smoke and the products of combustion leave the bucket by means of the open top 48 or by openings 44. Hollow metal sleeves 50 extend upwardly through openings in the bottom of the bucket and are held in vertical position by flanges 52 on the lower ends of the sleeves. Serrations or teeth on the flanges protrude into the plastic on the bottom of the bucket to secure the sleeves in place in the bottom of the bucket. Incense sticks 10 extend through the sleeves into the ground, if the ground is soft enough, or the sleeves themselves can support the incense sticks. This is important when the bucket is placed on frozen ground or an otherwise impenetrable surface.

Weather shield 40 also serves as a rain shield by simply turning the bucket over. In such a case, the incense sticks are inserted into the ground and the bucket is placed upside down over the sticks. Openings 44 thus serve as air inlets for combustion, and exhaust gases and smoke leave the bucket through openings 46 and through the openings in the sleeves 50.

An advantage of the weather shield 40 is that it protects the incense sticks from winds coming from all directions, which is a typical occurrence in the woods, where winds tend to swirl around and change directions from time to time. An added advantage of the bucket of weather shield 40 is that the combustion process occurs completely within the enclosed bucket and thus the risk of fire is further minimized.

As shown in FIG. 2, when an incense stick 10 is used without a protective weather shield, it is desirable that the stick be inclined slightly in a downwind direction. This prevents the wind from blowing directly on the glowing end of the stick and makes it more difficult for the wind to blow the burning stick out.

In operation, a hunter 60 places one or more sticks 10 in the ground preferably in a downwind direction, and ignites one or two sticks, blowing the initial flame out so the stick glows and smolders. The hunter then takes refuge in a blind 62 or tree stand. Deer 12 smell the aromatic smoke produced by the incense stick and are attracted to the hunter.

While the foregoing is illustrative of the preferred practice of the present invention, it should be understood that various modifications may be made in the arrangements and details of construction of the present invention without departing from the spirit and scope of the present invention, as defined in the appended claims.

I claim:

1. An animal lure comprising a combustible absorbent material that carries a fragrance material having a fragrance attractive to a specific animal being attracted, said fragrance material comprising the fragrance of urine of the animal that is being attracted, the animal lure being of restricted combustibility such that the absorbent material can be induced to burn and give off smoke without producing a continuous flame, the smoke entraining the fragrance with it as it travels through the air.

2. An animal lure according to claim 1 wherein the lure comprises an incense stick formed of a stick coated with the combustible absorbent material impregnated with the fragrance material.

3. An animal lure according to claim 2 wherein the incense stick is coated with a sufficient amount of combustible material and the flammability of the impregnated incense stick is low enough that the incense stick will burn for at least one-half hour under dry, still air conditions.

4. An animal lure according to claim 1 wherein the fragrance material comprises an aromatic substance that is dispersed in a liquid having a low volatility such that the liquid evaporates slowly at ambient temperatures but is vaporized readily at the temperatures encountered when the combustible material is burned, such that the liquid gives off its characteristic fragrance slowly and gradually as the combustible material is burned.

5. An animal lure according to claim 2 wherein the incense stick comprises a bamboo stick coated with a combustible, absorbent cellulose material formed from sawdust, the fragrance material comprising an aromatic oil admixed with a diluent, the aromatic oil comprising at least thirty percent (30%) by volume of the fragrance mixture.

6. An animal lure according to claim 1 and further comprising weather shield means for protecting the combustible material from at least the wind, the weather shield means comprising a container having enclosed side walls that surround the combustible material, the container having sufficient vent openings to provide adequate air for combustion, the container having smoke outlet means for releasing smoke from the container.

7. An animal lure according to claim 6 wherein the container comprises a plastic bucket having sidewalls, a bottom, and an open top, the vent openings being formed at a lower portion of the sidewalls, the bottom including at least one opening therethrough.

8. An animal lure according to claim 7 wherein the bucket further includes a hollow non-flammable sleeve mounted in the bucket and extending coaxially upwardly from the opening in the bottom of the bucket.

9. An animal lure according to claim 1 and further including weather shield means for protecting the combustible material from the wind and rain, the weather shield means comprising a baffle positioned at the side of the combustible material that shelters the combustible material from wind and rain shield positioned over the combustible material.

10. A human cover scent covering device comprising a combustible absorbent material impregnated with a fragrance material having a fragrance that masks the scent of humans, the scent covering device being of restricted combustibility such that the absorbent material can be induced to burn and give off smoke without producing a continuous flame, the smoke entraining the fragrance with it as it travels through the air.

11. A human cover scent covering device according to claim 10 wherein the cover scent comprises an incense stick formed of a stick coated with the combustible absorbent material impregnated with the fragrance material.

12. A human cover scent covering device according to claim 10 wherein the fragrance material comprises an aromatic substance that is dispersed in a liquid having a low volatility such that the liquid evaporates slowly at ambient temperatures but is vaporized readily at the temperatures encountered when the combustible material is burned, such that the liquid gives off its characteristic fragrance slowly and gradually as the combustible material is burned.

13. A human cover scent covering deviced according to claim 11 wherein the incense stick comprises a bamboo stick coated with a combustible, absorbent cellulose material formed from sawdust, the fragrance material comprising an aromatic oil admixed with a diluent, the aromatic oil comprising at least thirty percent (30%) by volume of the fragrance mixture.

14. A human scent covering device according to claim 10 wherein the scent covering device also functions as an animal lure, the fragrance material including a fragrance that is attractive to an animal.

15. An animal lure according to claim 1 wherein the fragrance material comprises a combination of fragrances, one being the fragrance of animal urine and another being a non-animal fragrance that softens the impact of the animal urine aroma.

16. An animal lure according to claim 15 wherein the other fragrance comprises an apple fragrance.

17. An animal lure according to claim 15 wherein the absorbent material comprises an incense stick.

18. An animal lure according to claim 15 wherein the lure comprises at least two incense sticks, one impregnated with a fragrance material comprising an animal urine fragrance and another impregnated with a fragrance material comprising a non-animal fragrance.

19. An animal lure according to claim 18 wherein the other fragrance comprises an apple fragrance.

20. An animal lure according to claim 1 wherein the animal is a deer and the fragrance material comprises the fragrance of deer urine.

21. An animal lure according to claim 1 wherein the fragrance material further comprises a food fragrance that the particular animal finds appealing.

22. An animal lure according to claim 21 wherein the food fragrance is one or more of the fragrances selected from the group consisting of apples, sweet corn, field corn, soy beans, red oak acorns, white oak acorns, peanut butter, anise, pumpkin, over-ripe apples, molasses, carrots, and dead fish.

\* \* \* \* \*